(12) United States Patent
Huang et al.

(10) Patent No.: US 9,040,273 B2
(45) Date of Patent: May 26, 2015

(54) ADSORPTION METHOD FOR IMMOBILIZING THE BIOMOLECULE AND THE BIOCATALYSIS SYSTEM USING THE ADSORPTION METHOD THEREOF

(71) Applicant: Chung Yuan Christian University, Zhongli, Taoyuan County (TW)

(72) Inventors: Hsi-Ya Huang, Zhongli (TW); Wan-Ling Liu, Houlong Township, Miaoli County (TW); Chia-Her Lin, Hsinchu (TW); Sheng-Han Lo, Zhuqi Township, Chiayi County (TW); Tadena Brenda Singco, Zhongli (TW); Chun-Chuen Yang, Taipei (TW)

(73) Assignee: Chung Yuan Christian University, Zhongli, Taoyuan County (TW)

( * ) Notice: Subject to any disclaimer, the term of this patent is extended or adjusted under 35 U.S.C. 154(b) by 0 days.

(21) Appl. No.: 14/140,298

(22) Filed: Dec. 24, 2013

(65) Prior Publication Data

US 2014/0342429 A1 Nov. 20, 2014

(30) Foreign Application Priority Data

May 16, 2013 (TW) .............................. 102117337 U

(51) Int. Cl.
*C12N 11/02* (2006.01)
*C12N 11/06* (2006.01)

(52) U.S. Cl.
CPC ...................................... *C12N 11/06* (2013.01)

(58) Field of Classification Search
USPC ....................................... 435/173.2, 177, 181
See application file for complete search history.

(56) References Cited

U.S. PATENT DOCUMENTS 6,825,032 B2 * 11/2004 Dapron et al. ............. 435/287.8
8,476,335 B2 * 7/2013 Huang et al. .................. 522/182

OTHER PUBLICATIONS

Wan-Ling L. et al. Novel Trypsin FITC@MOF Bioreactor Efficiently Catalyzes Protein Digestion. J of Materials Chemistry B vol. 1, 928-932, Jan. 8, 2013.*
Lu G. et al. Imparting Functionality to a Metal Organic Framework Material by Controlled Nanoparticle Encapsulation. Nature Chemistry vol. 4, 310-316, Apr. 2012.*
Wan-Ling Liu, et al., "Novel trypsin—FITC@MOF bioreactor efficiently catalyzes protein digestion", J. Mater. Chem. B, 2013,1, pp. 928-932.

* cited by examiner

*Primary Examiner* — Ralph Gitomer
(74) *Attorney, Agent, or Firm* — Muncy, Geissler, Olds & Lowe, P.C.

(57) ABSTRACT

A simple, highly efficient, and environmentally friendly method of immobilizing macromolecules, particularly the biomolecules, to a solid carrier and thus forming a bioreactor, including the following steps: (1) providing the biomolecule and a leading molecule, and linking the biomolecule and the leading molecule by microwave to form an adsorbent; (2) providing a porous support material, and mixing the porous support material and the adsorbent to form a mixture; (3) treating the mixture by a vortex process such that the adsorbent being adsorbed and immobilized on the porous support material to form a bioreactor for biological reactions and biocatalysis; and the bioreactor can be further used for constructing a biological reaction system via incorporating a buffer solution and a ligand.

7 Claims, 11 Drawing Sheets

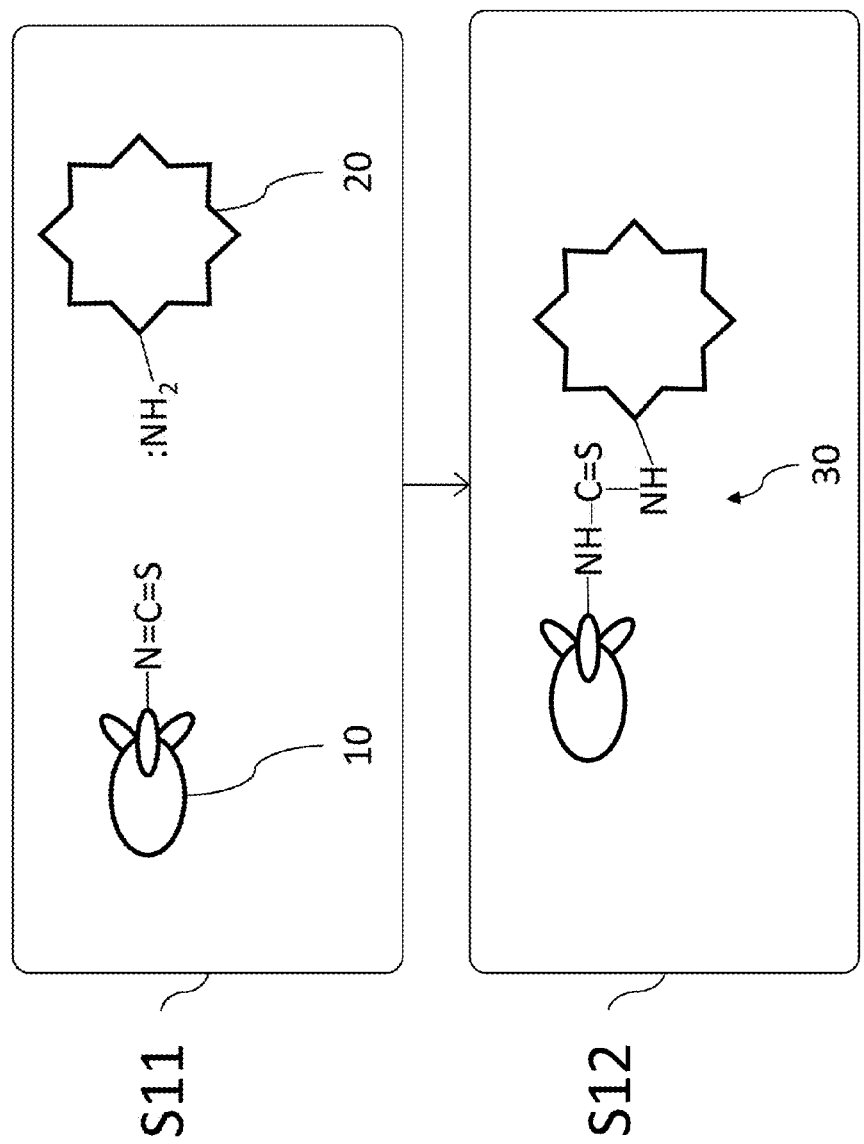

ADSORPTION METHOD FOR IMMOBILIZING THE BIOMOLECULE AND THE BIOCATALYSIS SYSTEM USING THE ADSORPTION METHOD THEREOF

CROSS REFERENCE TO RELATED APPLICATIONS

The present application is based on, and claims priority and the benefit from, Taiwan Application Serial Number 102117337, filed May 16, 2013, the disclosure of which is hereby incorporated by reference herein in its entirety.

FIELD OF THE INVENTION

The present invention relates to a molecule immobilization method, and more particularly to a biomolecule immobilization method and the biocatalysis system thereof. The present invention also relates to an adsorption method for immobilizing the biomolecule and the biocatalysis system using the adsorption method thereof.

BACKGROUND OF THE INVENTION

The metal organic frameworks (MOFs) are a highly crystalline complex compound constructed by specific materials. The MOFs usually form a coordination network in view of the microstructure. The coordination network is constituted primarily by "linkers" and "supportive clusters", wherein the supportive clusters are connected by the linkers. Generally, the linkers are organic molecules forming "organic ligands"; and the supportive clusters are metal ions or metal clusters. The organic ligands and the supportive clusters are connected to form the second-building unit (SBU). Thus, the coordination of the organic ligands and the supportive clusters, such as the dimensional distribution and orientation of the organic ligands and the supportive clusters as well as the way of bonding, significantly affects the material features and the porous characteristics. Therefore, by modulating the coordination of the organic ligands and the supportive clusters, the metal organic frameworks with specific properties can be manufactured. The porous characteristics give the metal organic frameworks vast potential of application, such as gaseous storage, gas separation, sensing, adsorption, separation and other conventional industrial applications. Moreover, the potential of the metal organic frameworks in biomedical application such as drug delivery becomes conspicuous.

Biocatalysis system usually utilizes natural catalysts such as enzymes and living cells to be the catalysts. Nowadays, the biocatalysis system has been widely used in chemical industry, food industry and pharmaceutical industry. In biocatalysis system using enzymes for catalysis, in order to achieve better catalysis efficiency, but the cost is higher and the activity of enzyme is unstable. Thus, immobilizing enzymes on solid support is an effective solution. For example, the widely used protease, trypsin, is usually applied for digesting the proteins into the small fragment peptides for proteomic analysis or industrial processes. Conventionally, digesting proteins with trypsin solution usually requires a time-consuming procedure taking 18 hours or more, which definitely results in an inefficient procedure. Recently, people try to immobilize the protease on the solid support (carrier) to improve the performance of enzyme-to-substrate ratio (can be expressed as [E]/[S]), reusability, high hydrolytic catalytic ability, reduced reaction time; such that the overall bio-catalytic performance can be improved.

Therefore, the quality of immobilizing enzymes on the solid carrier is significantly relevant to the actual performance of the biocatalysis system. Specifically, a suitable solid carrier is selected according to the specific enzyme and ligand system chosen for the biocatalysis, and then the specific enzyme is immobilized on the solid carrier, such that the enzyme can play the role of catalyst to exert it bio-catalytic activity in the biocatalysis system. Moreover, such biocatalysis system also works well in non-physiological environments conditions, which extends the versatile usage of the biocatalysis system. For example, intensifying or increasing the density (multi-points) of the covalent bonding between the enzyme and solid carrier can increase the rigidity of the enzyme such that the enzyme can stably exert the catalytic ability even in a relatively harsh environment, such as extreme temperature conditions or non-aqueous solvent environment. Nevertheless, inappropriate enzyme immobilization may alter the conformation and the function of the enzyme, and it will detract the enzyme catalytic performance.

Variant materials are used as solid carriers, and the most widely used solid carriers include nanoparticles, polymers, and inorganic compounds. The solid carriers are used to construct the bioreactor. According to the recent research results by S. Hudson et al. (Chem. Rev., 2012, 112, 724-781), they points out that the repeatedly used mesoporous silicates show enzyme leaching effect, so as to the practical use of the mesoporous silicates for performing the bio-catalytic function in an bioreactor is invalid. In addition, some researchers utilize the post-synthetic modification approaches to modify the materials; however, concerning the stability between the solid carrier and the enzyme, these approaches are still controversial and waiting to be verified.

On the other hand, the current methods of immobilizing enzymes on the solid carriers usually adopt the approach of linking the enzyme with the solid carrier by covalent bonding, but seldom adopt the "adsorption approach" for enzyme immobilization. However, the aforementioned covalent bonding method generally requires complicated functional group modification to fully achieve the firmly immobilizing the enzyme to the solid carrier, the more advanced study can be found in research paper from M. E. Medina et al. (Adv. Mater., 2011, 23, 5283-5292). In brief, when the user adopts the physical adsorption method, the "pore size" of the porous material of the solid carriers becomes a critical factor for stabilizing the enzyme immobilization. In other words, the pore size is subjected to the hydrodynamic diameter of the target biomolecule (e.g., enzyme) when the physical adsorption method is adopted, and the pore size is typically larger than 3 nm to 8 nm. In general, the porous material can be categorized into three types in view of pore size (pore diameter): microporous material with the diameter smaller than 2 nm; macroporous material with the diameter larger than 50 nm; and mesoporous material with the diameter ranging from 2 nm to 50 nm, which is between that of the microporous material and the macroporous material.

Thus, for the current application of biomolecules immobilization, achieving a porous structure with mesoporous pores is a basic criterion of the porous materials, which can be identified as the "mesoporous material". However, using the mesoporous material for the molecule adsorption or molecule immobilization usually needs complicated modification procedures (e.g., the chemical bonding or linking procedures) such that the mesoporous material can be more easily bonded with the biomolecule via chemical bonds, or adsorbed by the hydrophobicity attraction force, such that the biomolecules are immobilized or absorbed firmly on the mesoporous porous material. Thus, the absorption or immobilization can be improved for the specific biomolecule. The aforementioned "modification" procedures are unavoidably cumbersome and time-consuming, and additionally, the chemical processes of modification often consume large amounts of organic solvent and cause environmental problems.

On the other hand, whether the porous material can be widely applied for adsorbing or immobilizing specific molecules depends on the adsorption capability of the porous material for the molecules with different scales of sizes. At present, regarding the adsorption of larger size molecules (hereinafter referred to as macromolecules), such as the biomolecules of proteins, using the mesoporous material with oversized pore diameter results in the difficulty of retaining the macromolecules in the porous structure for further application procedures.

In response to the aforementioned technical demands of the porous materials, a few research results propose the concept and the technology of applying the metal-organic framework materials (MOFs) in biocatalysis system. The MOFs are used as the solid carrier or support for immobilizing the biomolecule in the biocatalysis system. For example, Y H. Shih et al. (ChemPlusChem., 2012, 11, 982-986), V. Lykourinou et al. (J. Am. Chem. Soc., 2011, 133, 10382-10385), Y. Chen et al. (J. Am. Chem. Soc., 2012, 134 (32), 13188-13191) respectively propose approaches to apply MOFs in biocatalysis system. Nevertheless, the aforementioned approaches or methods still relied on chemical bonding methods, which unavoidably have the aforementioned drawbacks of chemical bonding methods, such as complicated procedures, lengthy process, and environmental pollution threats.

Moreover, the presently available approaches for applying MOFs to immobilize macromolecules still have the disadvantages of significant morphological variations and small pores (usually less than 2 nm), which significantly limit the adsorption capability, separation ability or the macromolecule immobilization capability of MOFs. On the other hand, since the microporous material is so limited in the capability of adsorbing or immobilizing macromolecules, the knowledge of using the microporous material to adsorb the macromolecule is rare. Only few researches partially disclose the applications. For example, V. Lykourinou and Y. Chen, et al, propose methods of using microporous MOFs to physically adsorb macromolecule in the microporous structures of MOFs. However, although the microporous MOFs materials are used, regarding the size of the target molecule (macromolecules), the target molecule cannot fully enter the porous structure of microporous MOFs and thus cannot be retained therein. Thus, the adsorption is limited to a "surface adsorption". In addition, the adsorption of the aforementioned techniques is a lengthy process, which consumes about to 40 hours to 60 hours to complete the adsorption step and it is very time-consuming.

SUMMARY OF THE INVENTION

According to drawbacks of prior art as described above, the present inventors proposed a simplified, time-saving, and extensively applicable system for biological molecules adsorption and immobilization to overcome the problems of prior art.

The present invention provides a molecule immobilization method of immobilizing a biomolecule to perform a biocatalysis, the characteristics of the invention include:

(1) Providing the biomolecule and a leading molecule, and linking the biomolecule and the leading molecule by microwave to form an adsorbent.

(2) Providing a porous support material, and mixing the porous support material and the adsorbent to form a mixture.

(3) Treating the mixture by a vortex process such that the adsorbent being adsorbed and immobilized on the porous support material to form a bioreactor.

According to abovementioned molecule immobilization method, wherein the biomolecule is a protein enzyme including trypsin; the leading molecule is a small molecule dye including fluorescein isothiocyanate; and the porous support material is a metal organic framework.

According to above molecule immobilization method, the duration of linking the biomolecule and the leading molecule by microwave ranges from 1 minute to 5 minutes; and the duration of the vortex process ranges from 10 minutes and 60 minutes.

According to above molecule immobilization method, wherein the metal organic framework is an aluminum metal-organic framework material and the aluminum metal-organic framework material has a pore size ranging from 0.8 nm to 2.1 nm.

The present invention also provides a bioreactor which is characterized in that the bioreactor is formed by the aforementioned molecule immobilization method.

In addition, the present invention further provides a biological reaction system which is characterized in that the biological reaction system includes a buffer solution, a ligand and the bioreactor formed by the aforementioned molecule immobilization methods; wherein the bioreactor catalyzes the biocatalysis of the ligand, and the ligand includes lysine and arginine residue.

According to the concept of the molecule immobilization method, the bioreactor, and the biocatalysis system of the present invention, one of the objectives of present invention is to provide a simple, time-saving and effective molecule immobilization method. According to this method, the biomolecules can be guided by small leading molecules to be adsorbed and immobilized to the solid carrier with porous structure so as to form an effective bioreactor. And the bioreactor is further applied to perform the biocatalysis, wherein the protein ligands are catalyzed by the bioreactor.

Another objective of the present invention is to provide an integrated biocatalysis environment which is developed to construct a biocatalysis system.

Another objective of the present invention is to provide a biocatalysis system based on the aforesaid molecule immobilization methods and biocatalysis systems. The biocatalysis systems provide a simple, efficient, safe and environmental friendly way to achieve high performance biocatalysis and meanwhile to reduce the operation duration and costs. Furthermore, the biocatalysis systems and the materials used thereof are capable of repeatedly use, and the capability advantageously reduces the costs and avoids the problems derived from using, organic solvents, thereby improves the safety for operators.

BRIEF DESCRIPTION OF THE DRAWINGS

The present invention will be apparent to those skilled in the art by reading the following detailed description of a preferred embodiment thereof with reference to the drawings, in which:

FIG. 1A shows the principle and process of biomolecule immobilization method and the first step and second step of a preferred embodiment in accordance with the present invention;

DETAILED DESCRIPTION OF THE PREFERRED EMBODIMENT

Figure 1B:
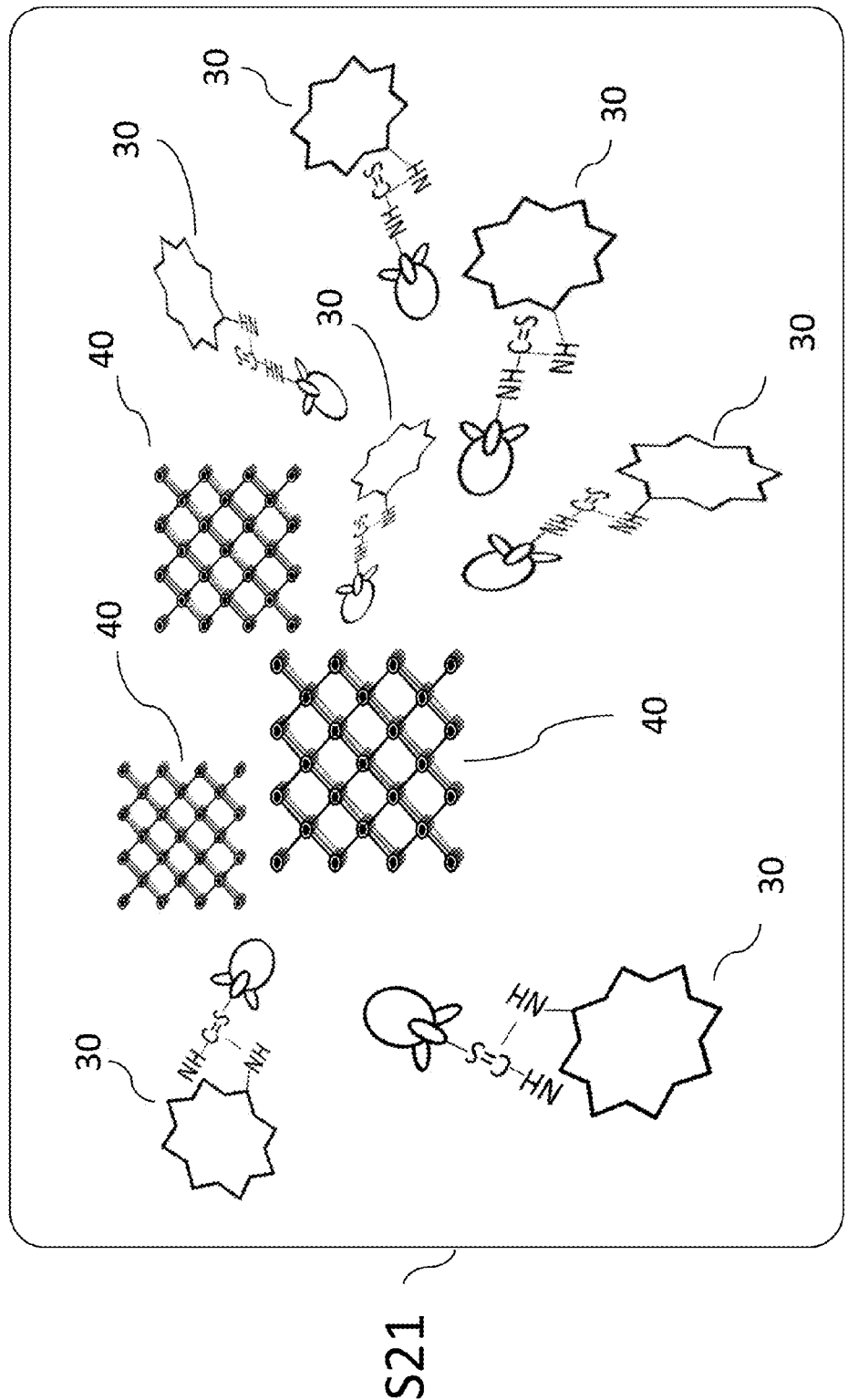
FIG. 1B shows the principle and process of biomolecule immobilization method and third step of a preferred embodiment in accordance with the present invention.

Certain example embodiments of this invention will now be described in more detail. Nevertheless, it should be recognized that the present invention can be practiced in a wide range of other embodiments besides those explicitly described, and the scope of the present invention is expressly not limited except as specified in the accompanying claims.

The present invention is based on utilizing the small molecule to diffuse effectively and to immobilize within the microstructure of porous support materials, such that the small molecule leads the macromolecule, especially for the biological macromolecule (refers to a variety of organic molecules existing in creatures with a general molecule weight of more than 10,000; such as proteins, enzymes, nucleic acids, lipids, carbohydrates and so on) to absorb and immobilize on the microporous material (can be regards as carrier carrier) made of metal organic frameworks (MOFs). Therefore, by such method, it becomes simple and effective to establish an efficient biocatalysis system and other related applications thereof. The following description details the technical features of the invention which will be described in certain embodiments.

Regarding constructing the solid carrier, approaches of absorbing and immobilizing the biomolecules in the microporous material usually involves the step of chemical bonding methods, and the adsorption efficiency of chemical bonding methods vary in accordance with the type of modification. Normally, the adsorption time is tedious and time-consuming. On the other hand, approaches using physical adsorption methods typically utilize the attraction force between the molecules of target biomolecules and the molecules of the microstructure to achieve the adsorption and immobilization. The physical adsorption process does not involves the substantial condition of electron transfer, generation or broken of the chemical bonds, and atoms reorganization, and thus, ideal adsorption efficiency can be acquired. The adsorption performance normally depends on the interactions between the biomolecule and the solid carrier on the basis of their physical characteristics (such as the conformability between the pore size and the target biomolecule size, and the interaction force between the molecules).

Regarding the application of the biocatalysis system, in order to obtain the better catalysis and reaction performance, the porous support material of the solid carrier used to immobilize the biocatalyst (especially proteases) preferably has the those advantageous properties including: (1) appropriate pore size to match the size of the target molecules to be adsorbed; thereby the large surface area can increase the amount of the immobilization; (2) appropriate the micro-environment of the microporous structure for firmly adsorbing the target molecule to prevent the leaching effects; (3) stable and the intact framework integrity for stabilizing the reaction and for regeneration.

Thus, the microporous materials of the present invention are preferably MOFs that include above-identified advantageous properties. Moreover, because various MOFs are available, the structure of MOFs is easy to modulate flexibly as required, the pore sizes of MOFs are relatively uniform, and MOFs has high surface area features due to the porosity, the MOFs with microporous structure are more preferably for practicing the present invention.

Fluorescein isothiocyanate (hereinafter referred to as FITC) is a widely used biomolecule fluorescent dye, which possesses the excellent fluorescence marking performance. FITC is widely applied for tagging biomolecule for detection. Because FITC has excellent fluorescent performance (i.e., transferring the excitation energy into fluorescent emission), FITC are extensively used for marking/tagging enzymes or other biomolecules to detect or locate the target biomolecules via the fluorescent labeling. The molecule weight of the FITC is 389 Dalton (Da), which is regarded as a very small molecule. Therefore, when FITC is linked with the protein molecules (such as enzyme and antibodies), typically multiple FITC molecules are linked with each protein molecule. FITC is a highly reactive nucleophile, and thus FITC can easily react with the nucleophilic groups such as amine groups and sulfhydryl groups in protein for chemical linkage or bonding. The small molecule size of makes FITC easily and accurately link with protein molecules. Thus, FITC is preferably chosen to be the leading molecule for practicing the molecule immobilization method according to the present invention.

However, it is should be noted that, in addition to FITC, other small molecules with small molecule size which can be easily linked with protein molecules are applicable to the present invention. Thus, the type of the leading molecule is not limited in the present invention.

Among biocatalysis systems, protein enzymes are most widely used. Since the present invention does not involve the complicated chemical modifications, the highly specific modification steps are avoided. Consequently, the method of the present invention is applicable for all types of enzymes macromolecules. In other words, the method of the present invention are suitable for extensive uses, which is not limited to particular types of enzymes, thereby any protease having bio-catalytic activity can be applied to form the bioreactor or the biocatalysis system according to the present invention.

In order to illustrate the features of the present invention, the present invention provides a "trypsin biocatalysis system" for the preferred embodiment. Currently, trypsin biocatalysis system has been widely used in proteomic analysis and industrial application, and the detail catalytic principle and the usage is known to those skilled in the art, and therefore is not described in detail herein. In short, as to the usage in "proteomics analysis", trypsin is easy to be purified in large scale, large amount of the trypsin can be obtained. And the extensive application methods, stable activity, and digestion accuracy of trypsin makes trypsin biocatalysis system an ideal system to digest macromolecule proteins into small fragment peptides suitable for mass spectrometry. As to the usage in the industrial application, trypsin can be used to process natural materials such as degreasing and degumming, thereby trypsin is widely used in tanning (to soften the leather and enhance the quality of leather), silk printing and dyeing (to simplify the processes and shorten the catalytic time), food and other industries.

Accordingly, the present invention is based on the aforementioned principles and provides a novel method and biocatalysis system thereof for adsorbing, and immobilizing the biological macromolecules, which utilizes the small molecules as the leading molecules to be linked with the biological macromolecules. Then the leading molecules acquire sufficient energy to lead the biological macromolecules to diffuse toward the MOFs and finally the leading molecules enter the microporous structures of MOFs and thereby the macromolecules are firmly adsorbed to the solid carrier constructed by MOFs. In this way, the biological macromolecules can be immobilized to the solid carrier in a simple and effective manner.

The method of the present invention not only simplifies the operation process, but also eliminates many drawbacks of the chemical bonding methods. When accompanied by the advantages of high surface area of MOFs, the method of the present invention allows a large number of biological macromolecule to immobilize to the solid carrier intensively and effectively and enhance the catalytic efficiency of the biocatalysis and the overall reaction performance. Moreover, the biocatalysis system according to the present invention further includes regeneration property of reusability. A preferred embodiment of the present invention is demonstrated herein, in the preferred embodiment, FITC is used as the leading molecule to link with trypsin, and FITC leads trypsin to be adsorbed and immobilized to MOFs to form a trypsin bioreactor as well as an improved trypsin biocatalysis system; meanwhile, the superior biocatalysis performance is validated by using the trypsin biocatalysis system.

According to aforementioned contents relate to the present invention, a biomolecule immobilization method of immobilizing a biomolecule to perform a biocatalysis is provided; and more particularly, the biocatalysis is an enzyme catalytic reaction. A preferred embodiment of the present invention is provided herein to illustrate the steps of the biomolecule immobilization method. When accompanied by the interpretative drawings, the following descriptive contents fully illustrate the technical feature and the advantageous effects of the present invention.

First, the biomolecule immobilization method of the present invention is provided for various type of biocatalysis (for example, biomolecule adsorption, enzyme catalytic reaction), and the types of the biomolecule is not limited herein. The biomolecule immobilization method includes the following steps. Step S1 denotes that the biomolecule and the leading molecule having bio-catalytic activity are treated with microwave process to linking the biomolecules with leading molecules to form an absorbent. Typically, one biomolecule can link with multiple leading molecules. The biomolecule includes protein, enzyme or other biomolecule for adsorption, wherein the biomolecule is preferably a protease; the leading molecule is protein dye or labeled substance which is required to be a small molecule (preferably the volume of the molecule is smaller than $2\times2\times2$ nm$^3$ or smaller than 10 nm$^3$) and to be capable of being easily linked with the protein molecules or with the function groups such as amine groups and sulfhydryl groups of proteins. More preferably, the biomolecule is trypsin and the leading molecule is FITC.

Then, refer to FIG. 1A to FIG. 1E showing the preferred embodiment of the biomolecule immobilization method of the present invention. Refer to FIG. 1A which illustrates the steps S11 and S12 according to the preferred embodiment of the present invention. In step S11, the biomolecule (trypsin) 20 is first provided and is mixed with the leading molecule (FITC) 10 sufficiently. Then, the biomolecule (trypsin) 20 is linked with the leading molecule (FITC) 10 by microwave process for further conducting step S12. In Step 12, the biomolecule (trypsin) is linked with at least one leading molecule (FITC) 10. Trypsin 20 can be prepared by purification or by commercially available products, as long as trypsin 20 with trypsin enzymatic activity of cleavage, and the trypsin 20 it is not limited to the full-length trypsin. Other source of trypsin 20 can be obtained by artificially cloning, modifying or improving the active fragment of trypsin 20. As to the FITC 10, the commercially available products FITC are preferable for the convenience. The duration of linking the biomolecule and the leading molecule by microwave ranges from 1 minute to 5 minutes, and the preferable duration ranges from 1.5 minutes to 2.5 minutes.

Because the trypsin 20 contains amine groups and sulfhydryl groups and the significant difference of molecule size between FITC 10 and trypsin 20, typically a single trypsin molecule 20 can link with at least one FITC molecule 10. This principle can be applied to other enzyme. Thus, the percentage of the biomolecule (trypsin) 20 and the leading molecule (FITC) 10 in view of the quantity of molecules is not to be limited. Practically, according to the preferred embodiment of the present invention, a single trypsin 20 is generally linked with one or more FITC 10 to form the adsorbent 30.

Refer to FIG. 1B which illustrates the step S21 according to the preferred embodiment of the present invention. The porous support material (MOF) 40 with porous structure is provided and is mixed with the absorbent 30 to form a mixture to make the porous support material 40 and the absorbent 30 dispersed in the mixture uniformly. The type of porous support material 40 is preferably MOF but the type of MOF is not limited herein. As long as the pore size of MOF is substantially appropriate for the adsorption of leading molecule 10, various MOFs can be chosen for conducting the method of the present invention. Thus, the pore size of the porous support material MOF 40 ranges from 0.8 nm to 2.1 nm according to the leading molecule FITC; and the pore size of the porous support material MOF 40 is preferably ranges from 1.5 nm to 2.1 nm.

Figure 1C:
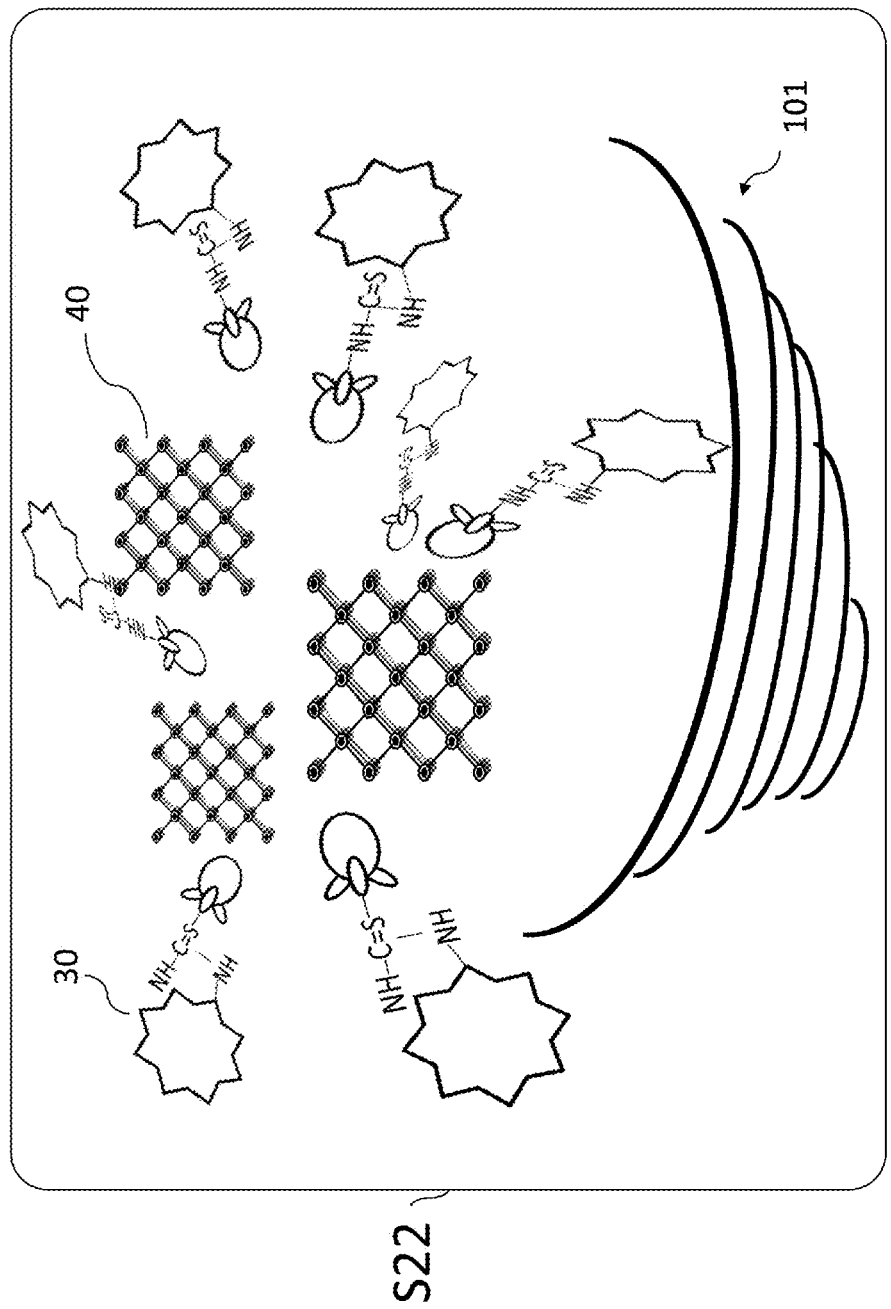
FIG. 1C shows the principle and process of biomolecule immobilization method and fourth step of a preferred embodiment in accordance with the present invention.
Figure 1D:
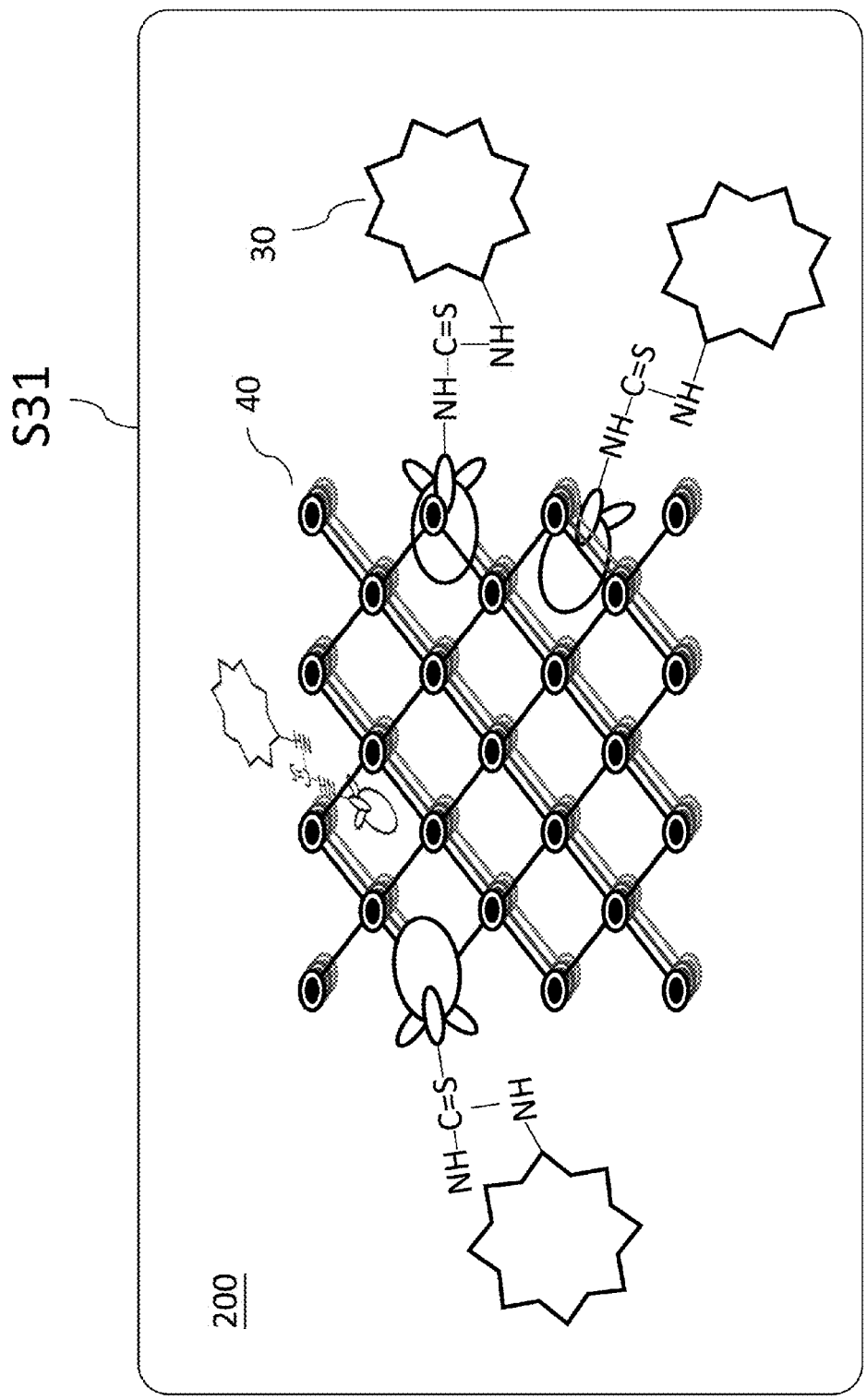
FIG. 1D shows the principle and process of biomolecule immobilization method and fifth step of a preferred embodiment in accordance with the present invention.

Refer to FIG. 1C which illustrates step S22 according to the preferred embodiment of in the present invention. The mixture containing porous support material MOF 40 and absorbent 30 is treated by a vortex process 101. The vortex process 101 provides the energy required for the absorbent 30 to be adsorbed to the porous support material MOF 40. In other words, refer to step S31 as shown in FIG. 1D, the energy required for the host-guest interaction and the adsorption between the absorbent 30 and the porous support material MOF 40 can be obtained from the simple vortex process 101. By the leading of the small leading molecule (FITC) 10, the biomolecule (trypsin) 20 is driven into the porous support material MOF 40 to make the absorbent 30 being absorbed firmly and then immobilized to the porous structure of the porous support material MOF 40, and the absorbent 30 are mainly adsorbed inside the porous structure. The immobilized absorbent 30 and the porous support material MOF 40 as a whole form the bioreactor 200. The operation time/duration for the vortex process ranges from 10 minutes to 60 minutes, and preferably ranges from 15 minutes to 40 minutes.

Figure 1E:
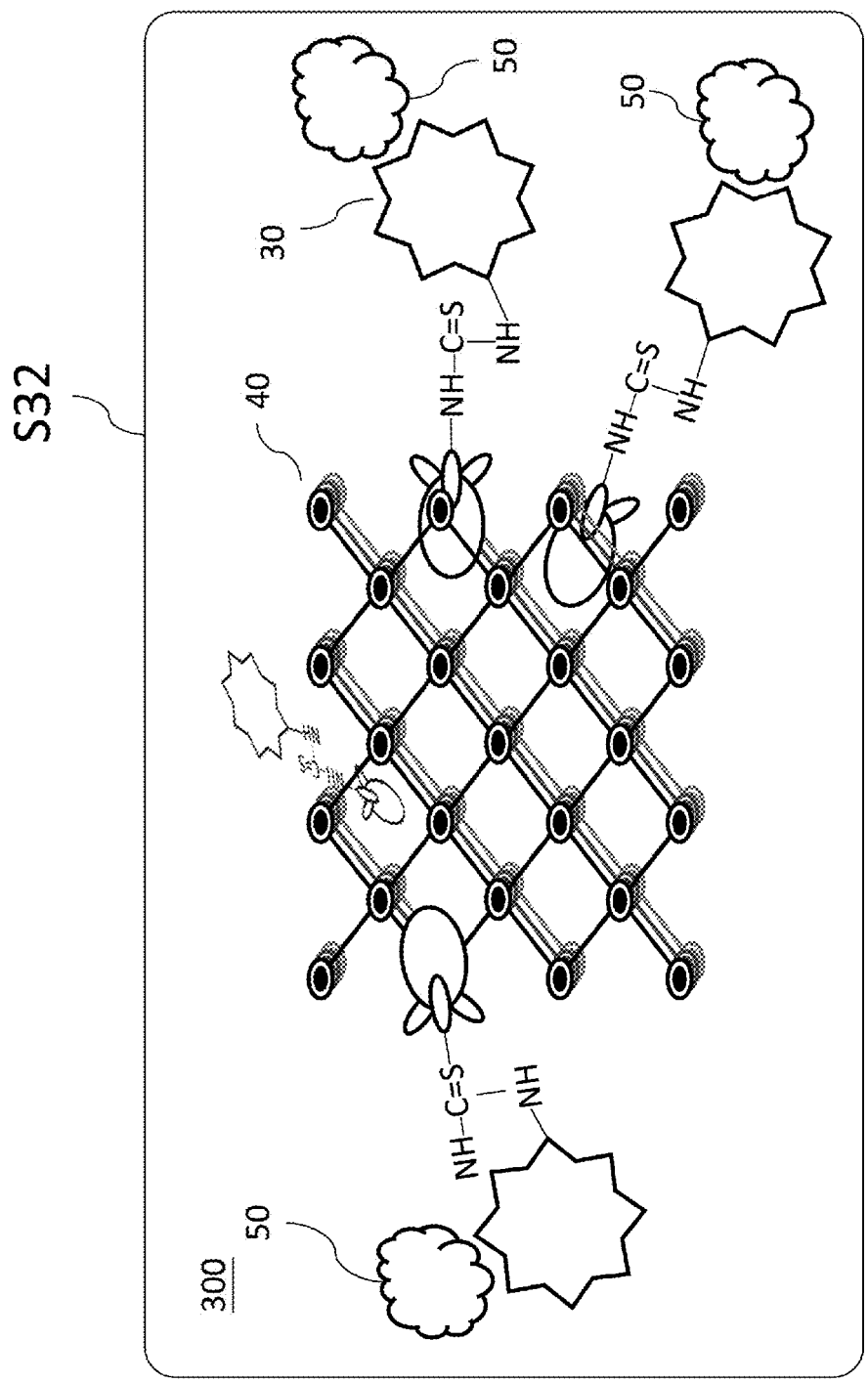
FIG. 1E shows the principle and process of biomolecule immobilization method and sixth step of a preferred embodiment in accordance with the present invention.

Further refer to FIG. 1E which illustrates step S32. In step S32, a biocatalysis is performed by a bioreactor constructed by trypsin, FITC, and MOF. The biocatalysis and the catalytic reaction between the trypsin and the ligand of the trypsin are well-known to those skilled in the art and is not repeated herein. The type of the ligand 50 of trypsin is not limited herein. According to the known characteristics of the trypsin and the developed application, the ligand 50 according to the preferred embodiment is protein or peptide contains Lysine and Arginine residues. The ligand 50 can be flexibly selected according the user's demands to match the trypsin 20 used. For example, the bovine serum albumin (BSA) is commonly used to detect the trypsin activity. Therefore, embodiments of the present invention also utilize BSA as the standard ligand for evaluating the activity of trypsin to fully illustrate the characteristic, features and the resultant advantageous effects of the present invention.

As shown in step S32, the bioreactor 200 formed by the biomolecule immobilization method according to the present invention is further used for establishing a biocatalysis system 300. Specifically, an appropriate buffer system is adopted to provide the biocatalysis environment for the bioreactor 200 and ligand 50, wherein the bioreactor 200 is responsible for conducting the biochemical reaction or catalytic reaction of the ligand 50. Hence, a functionally effective biocatalysis system 300 is established to be widely used in accordance with the application of trypsin.

Obviously, comparing to the conventional solid carrier or porous support material prepared by chemical bonding modification method, the present invention provides an effective, simple, and environmentally friendly method of biomolecule immobilization method. Thus, according to the biomolecule immobilization method of the present invention, the target biomolecule can be immobilized to the solid carrier effectively to improve the biocatalysis performance. And the bioreactor as well as the biological reaction system according to the present invention consistently exert the advantageous effects The MOFs used for the present invention is not limited herein. Based on the microporous properties of MOFs, FITC with small molecule size (the molecule size is 0.9×1.2×1.4 $nm^3$) can easily enter into the microporous structure of MOFs. Nevertheless, the disclosure regarding the application of MOFs in the adsorption of small dye molecule FITC is rare currently, and no research has been done to elucidate the adsorption pattern of FITC to the MOFs. Therefore, to solve the above-identified problems, the present invention first provides the advantageous adsorption patterns between FITC and a variety of MOFs, and the advantageous effect would be interpreted in the following description.

Specifically, MOFs of the present invention includes MIL-88B(Cr), MIL-53(Al), MIL-53(Cr), DUT-4(Al), MIL-101(Cr), DUT-5(Al), and CYCU-4, and the properties related to the porous structure are listed in Table 1. Meanwhile, the capabilities of capturing or absorbing FITC of aforesaid various MOFs are analyzed. FITC (5 mM), the MOFs, sodium carbonate buffer solution (100 mM) are mixed to perform an FITC absorbing test to determine the capabilities of capturing or absorbing FITC of the various MOFs. The results of the analysis are shown in Table 1.

TABLE 1

Pore size, FITC absorption and BSA digestion efficiency of MOFs

| MOFs | Chnannel size (nm) | FITC absorption (%) | $1^{st}$ Sequence coverage (%) | $2^{nd}$ Sequence coverage (%) |
|---|---|---|---|---|
| MIL-88B(Cr) | — | 0 | —[b] | —[b] |
| MIL-53(Al) | 0.8 × 1.1 | 0 | 22 | 14 |
| MIL-53(Cr) | 0.9 × 1.1 | 17 | —[b] | —[b] |
| DUT-4(Al) | 1.0 × 1.4 | 99 | 38 | —[c] |
| MIL-101(Cr) | 1.2 and 1.6 | 100 | 56 | 54 |
| DUT-5(Al) | 1.4 × 1.7 | 92 | 55 | —[c] |
| CYCU-4 | 1.6 × 2.2 | 94 | 72 | 71 |
| "Al$_{(III)}$ + H$_2$SDC"[a] | — | 7 | 39 | 4 |

[a]The synthesized amorphous material was prepared from a mixture of the same metal ion and organic linker used for CYCU-4 via 24 h stirring at room temperature.
[b]No BSA digests were measured.
[c]MOFs decomposed at first reuse.

Table 1 shows that the channel sizes (also called the windows) of MIL-53 (Al) and MIL-53 (Cr) range from 0.8 nm to 1.1 nm, and the absorption capabilities are relatively poor with less than 17% FITC absorption. The channel sizes for MIL-101 (Cr) and DUT-4 (Al) are about 1.2 nm, and the both present the exhaustive absorption capabilities with more than 99% FITC absorption. The channel sizes between DUT-5 (Al) and CYCU-4 are larger than 1.4 nm with 92%-94% FITC absorption. The analysis result shows the relationship between the FITC absorption capabilities of and channel size of MOFs. In addition to MIL-88B (Cr), MIL-53(Al), and MIL-53(Cr), the aforesaid channel sizes (1.2 nm-2.1 nm) of MOFs are larger than the molecule size of FITC (0.9×1.2×1.4 $nm^3$), which allow large amount of FITC to enter into the pore, so that the MOFs capture FITC by the π-π interaction between and organic ligands and FITC and the hydrogen bonds. According to FITC absorption test results for above MOFs, MOFs with better FITC absorption performance are selected to be the porous support materials for the solid carriers. According to the biomolecule immobilization method of the present invention, the selected MOFs are used for immobilizing the trypsin by adsorption and the selected MOFs are prepared to obtain specific bioreactors respectively. The adsorption efficiency of the assayed bioreactors is shown in Table 2.

TABLE 2

Adsorption efficiency of bioreactor

| MOFs | Incubation time | Consecutive digestion | Sequence coverage (%) | Matched peptides |
|---|---|---|---|---|
| Trypsin-FITC | 18 h | $1^{st}$ | 49 | 24 |
|  | 2 min | $1^{st}$ | 72 | 44 |
| MIL-53(Al) | 2 min | $1^{st}$ | 22 | 9 |
|  |  | $2^{nd}$ | 14 | 7 |
| DUT-4(Al) | 2 min | $1^{st}$ | 38 | 21 |
|  |  | $2^{nd}$ | — | — |
| MIL-101(Cr) | 2 min | $1^{st}$ | 55 | 28 |
|  |  | $2^{nd}$ | — | — |
| DUT-5(Al) | 2 min | $1^{st}$ | 56 | 37 |
|  |  | $2^{nd}$ | 54 | 30 |
| CYCU-4 | 18 h | $1^{st}$ | 52 | 27 |
|  | 2 min | $1^{st}$ | 72 | 47 |
|  |  | $2^{nd}$ | 71 | 40 |
| "Al$_{(III)}$ + H$_2$SDC" (non-porous) | 2 min | $1^{st}$ | 39 | 22 |
|  |  | $2^{nd}$ | 4 | 2 |

In addition, the linkage between of FITC and trypsin is based on that the nucleophilic isothiocyanate group of FITC attacks the amine groups of trypsin. Thus, a brief heating process of around 2 minutes by microwave is sufficient to link FITC with trypsin in the mixture to form a FITC-labeled trypsin which is the aforesaid "absorbent". And the duration of microwave heating is preferably about 2 minutes. The "absorbent" is hereinafter referred to as "Trypsin-FITC" for brevity. Thus, when Trypsin-FITC is treated with vortex process for about 60 minutes by aforesaid biomolecule immobilization method of the present invention, sufficient energy are provided to immobilize the Trypsin-FITC to specific MOF to form a "bioreactor", and the bioreactor is hereinafter referred to as "Trypsin-FITC@MOF", in which the practically used MOF can be replaced or adjusted according to the user demands. Furthermore, when the absorbent "Trypsin-FITC" and MOF are treated with the vortex process, are the immobilization process of the Trypsin-FITC to the MOF, and the duration time required to accomplish the immobilization process can be regards as "immobilization time".

The activity of the Trypsin-FITC or the Trypsin-FITC@MOF bioreactor on the ligand (i.e., hydrolysis or cleavage of the specific peptide bonds), which also substantially represents the performance of the "biocatalysis system" according to the present invention. In order to determine the activity of the Trypsin-FITC or the Trypsin-FITC@MOF, bovine serum albumin (BSA) is used as the standard ligand for evaluating the activity of the free form Trypsin-FITC or Trypsin-FITC@MOF. The approach for assaying the activity is base on detecting the product of the reaction between the functional trypsin and BSA. The hydrolyzed (or digested) peptide fragments are detected by nanoLC-MS method (commonly used for identifying and analyzing of hydrolyzed peptide fragments). The data are further analyzed according to Mascot database (a database of mass spectrums and sequences for aligning and identifying proteins or peptides). Based on the aforesaid approach, the hydrolytic activity of trypsin is determined; and the results of analysis are represented by the ratio of "sequence coverage". The results of related analysis are shown in Table 1 and Table 2.

Figure 2:
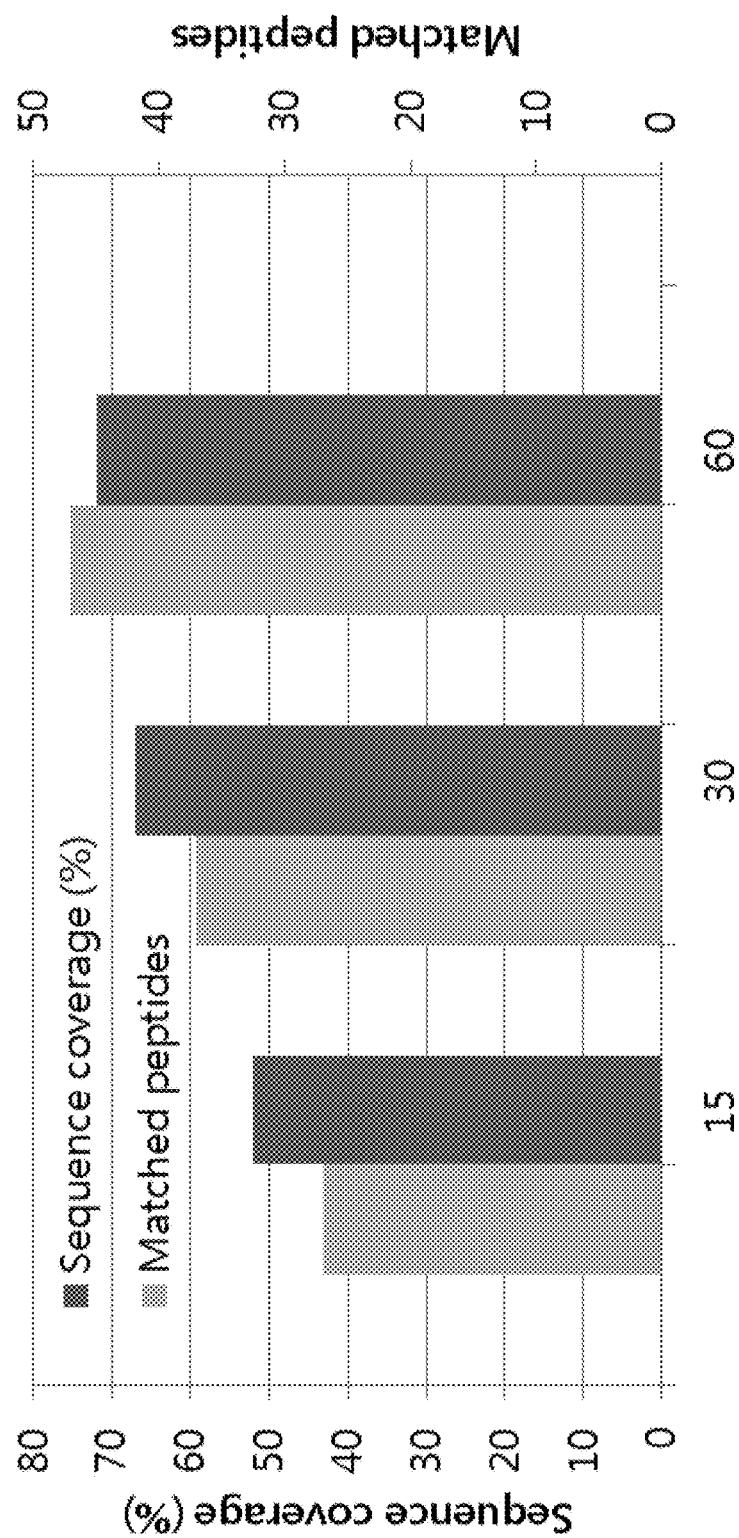
FIG. 2 is a diagram of the bio-catalytic performance of a bioreactor prepared by the simple vortex process provided by the present invention, wherein the diagram shows the efficiency of hydrolyzing protein by the bioreactor.

Refer to Table 1 and Table 2, the results show that Trypsin-FITC is capable of hydrolyzing BSA into 43 peptide fragments, and the ratio of sequence coverage is 72%. As to the performance of Trypsin-FITC@MOF, when "CYCU-4" is used as the MOF for preparing the bioreactor named Trypsin-FITC@CYCU-4, Trypsin-FITC@CYCU-4 is capable of hydrolyzing BSA into 47 peptide fragments, and the ratio of sequence coverage is 72%. In addition, the effects of immobilization time on the hydrolytic activity of trypsin are further analyzed by adjust the time duration of vortex process, and the result are shown in FIG. 2. When the duration time of vortex process is reduced to be 15 minutes, Trypsin-FITC@CYCU-4 is capable of hydrolyzing BSA into 27 peptide fragments, and the ratio of sequence coverage is 52%. When the duration time of vortex process is reduced is reduced to be 30 minutes, Trypsin-FITC@CYCU-4 is capable of hydrolyzing BSA into 37 peptide fragments, and the ratio of sequence coverage is 67%. As observed in other proteomic analysis method, when BSA is used as a ligand for trypsin, the urea in solution environment can affect the stability of the disulfide bonds of BSA such that BSA may be slightly degraded slightly prior to the actual hydrolysis process, however, the data interpretation would not be interfered under well-controlled conditions.

Therefore, according to above results, either the specific active sites or the activity of the trypsin of trypsin is not interfered by the labeling FITC on trypsin. Moreover, after the Trypsin-FITC being adsorbed to MOF, the orientation of adsorption does not affect the activity of trypsin. Obviously, the small leading molecule FITC leads the trypsin to be adsorbed and immobilized to MOFs to form a bioreactor, and the bioreactor still maintains the activity of trypsin to hydrolyze BSA (the sequence coverage is 22%-72%). And the overall biocatalysis performance can be further improved with the increase of pore size or channel size.

Concerning the enzyme leaching effects evoked by repeatedly using the bioreactor of conventional solid carriers, the regeneration for the most solid carrier is significantly limited. To solve this problem, the present invention provides the biomolecule immobilization method to achieve the bioreactor and the biocatalysis system which are advantageously reusable. The reusable bioreactor avoids the drawbacks as discussed above. The so-called "reusable" is identified as the bioreactors or biocatalysis system can maintain its performance even when the materials undergo repeatedly use or operation. Based on the above definition, the aforesaid MOF bioreactor contains DUT-4 (Al) and DUT-5 (Al) (see Table 2) has no data for second sequence coverage ratio of second hydrolysis. The reason for the unavailable second hydrolysis for the bioreactor contains DUT-4 (Al) and DUT-5 (AL) is that both bioreactors become mash and rapidly dissolve in the sodium carbonate solution after the first hydrolysis such that both bioreactors are difficult to reuse.

Particularly, according to the aforementioned bioreactors of MOF, Trypsin-FITC@CYCU-4 bioreactor and Trypsin-FITC@MIL-101(Cr) bioreactor not only have excellent hydrolytic activity against BSA (the sequence coverage is 72% and 56% respectively) but also have the capability of regeneration for reuse. Practically, Trypsin-FITC@CYCU-4 bioreactor can be repeatedly used for at least 5 times and Trypsin-FITC@MIL-101(Cr) bioreactor can be repeatedly used for at least 2 times. Furthermore, both Trypsin-FITC@CYCU-4 and Trypsin-FITC@MIL-101(Cr) bioreactors maintains their performance on reaction efficiency and consistency. Consequently, Trypsin-FITC@CYCU-4 bioreactor and Trypsin-FITC@MIL-101(Cr) bioreactor are the preferable implementation types of the present invention.

TABLE 3

Efficiciency of consecutive digestion of preferable bioreactors

| MOF | Consecutive digestion | Sequence coverage (%) | Matched peptides |
|---|---|---|---|
| Trypsin-FITC@CYCU-4[a] | 1st | 72 | 47 |
|  | 2nd | 71 | 39 |
|  | 3rd | 65 | 38 |
|  | 4th | 70 | 40 |
|  | 5th | 63 | 37 |
| Trypsin-FITC@MIL-101(Cr)[b] | 1st | 56 | 37 |
|  | 2nd | 54 | 30 |
|  | 3rd | —[c] | — |

[a]1st batch synthesized CYCU-4 used as trypsin-immobilized MOF bioreactor;
[b]1st batch synthesizedMIL-101(Cr)used as trypsin-immobilized MOF bioreactor;
[c]No BSA digests were measured Accordingly, the following are the preferred embodiments of the present invention utilizing the preferable CYCU-4 and MIL-101(Cr) materials. The characteristics and the related property analysis of CYCU-4 and MIL-101(Cr) materials are detailed with the description to illustrate the present invention.

Embodiment 1

Preparation and Characterization of CYCU-4

CYCU-4 is an inexpensive composite material which can be easily prepared. CYCU-4 is an aluminium based microporous MOF, Al(OH)(SDC), the molecular formula is $Al_4O_{20}C_{64}H_{44}$ which is fabricated via using commercially available and inexpensive materials. More specifically, CYCU-4 has aluminum based MOF microporous characteristics, and CYCU-4 can be modulated to form mesopores by aqueous solution immersion method. As to the preparation (synthesis) of CYCU-4, the strategy is to construct an infinite number of rod-shaped aluminum carboxylate secondary building units and use a linear organic ligand, 4,4-stilbenedicarboxylic acid ($H_2SDC$), as linker forming Al(OH)(SDC) (i.e., CYCU-4). CYCU-4 was synthesized under solvothermal conditions. This $H_2SDC$ ligand has a longer length (13.7 Å) than common linear organic O-donor ligands that may potentially be used to construct mesoporous MOFs.

Practically, the procedure of synthesizing CYCU-4 is described as below. A reaction mixture of $H_2SDC$ (0.097 g, 0.36 mmol), $Al(NO_3)_3 \cdot 9H_2O$ (0.176 g, 0.47 mmol), and N,N-diethylformamide (DEF) (10.0 ml) is stirred for 5 min at room temperature, forming a homogeneous solution. The solution is heated at 180° C. for 3 days. A pale-yellow powder is filtered off, washed with dimethylformamide (DMF), dried at 120° C. in an oven, and collected, yielding a CYCU-4 product weighing 0.1947 g.

Figure 3:
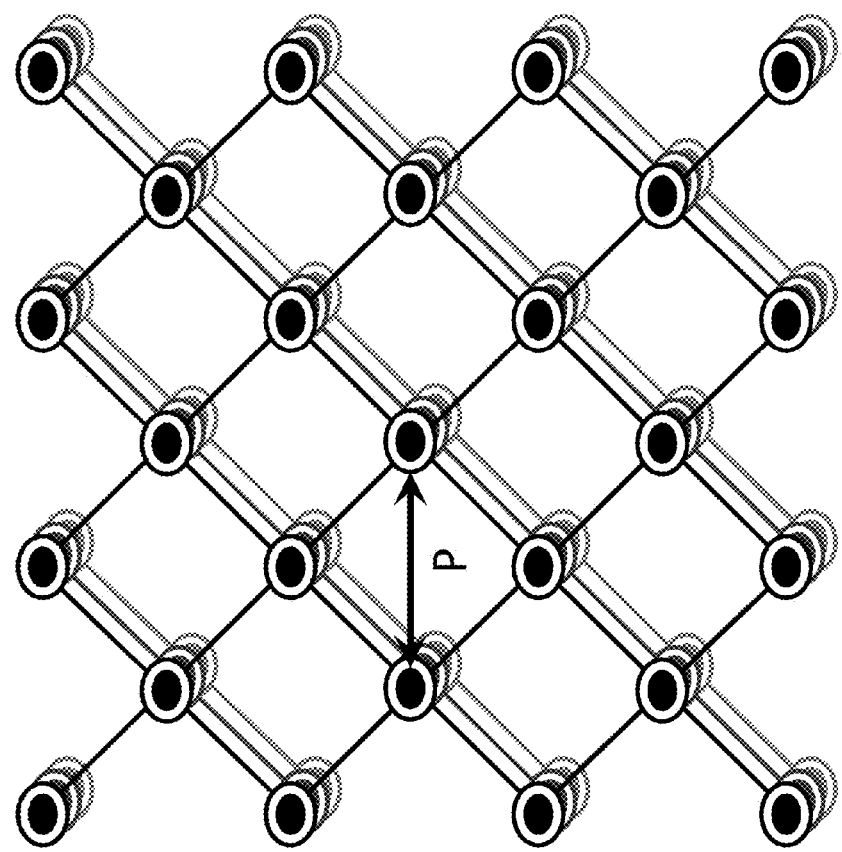
FIG. 3 is a diagram showing the three-dimensional porous structure of a solid carrier of a preferred embodiment in accordance with the present invention.
Figure 4:
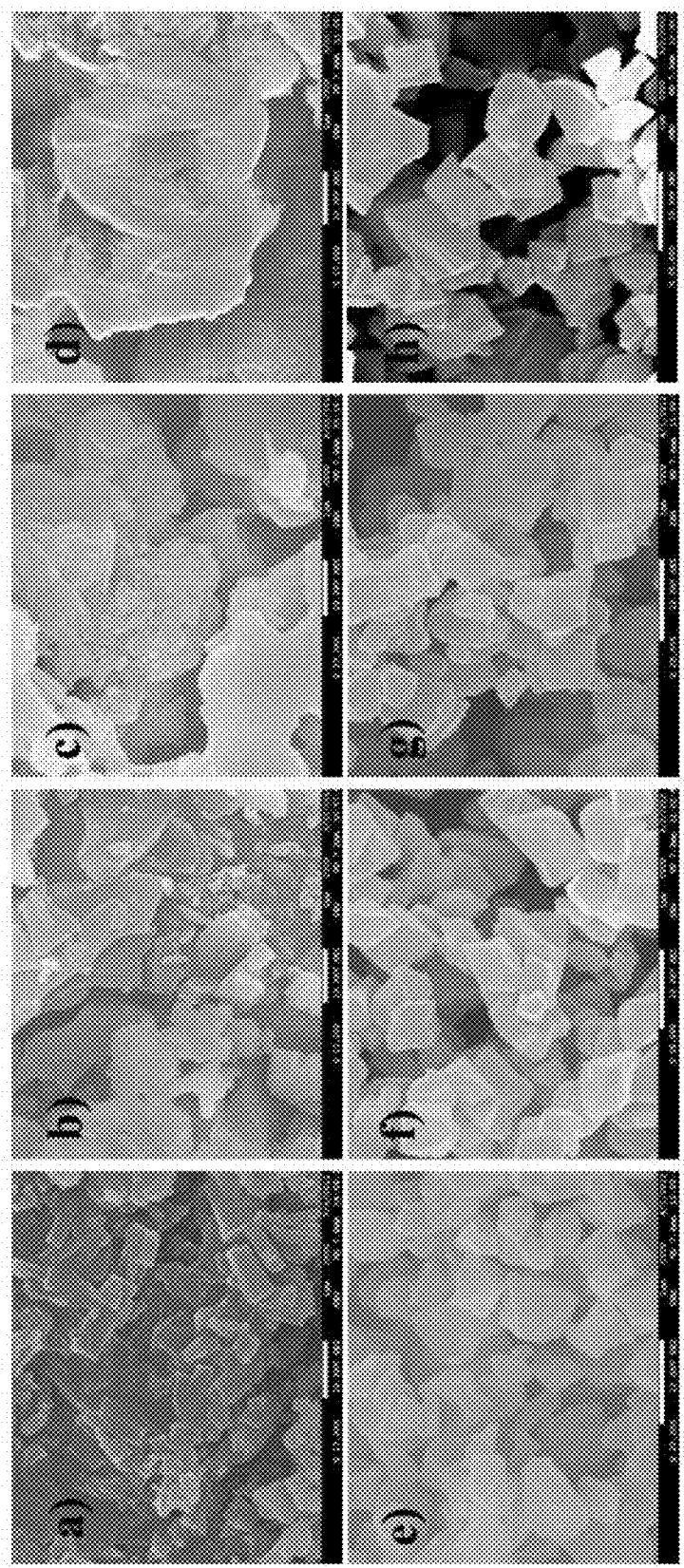
FIG. 4 shows images of scanning electron microscopy (SEM) which shows the appearance of porous support material CYCU-4 and MIL-101(Cr) at different stages of biomolecule immobilization method according to a preferred embodiment of the present invention. (a) CYCU-4 synthesis product; (b) dried CYCU-4 after being soaked in sodium carbonate solution; (c) FITC@CYCU-4; (d) Trypsin-FITC@CYCU-4; (e) MIL-101(Cr) synthesis product; (f) dried MIL-101(Cr) after being soaked in sodium carbonate solution; (g) FITC@ MIL-101(Cr); (h) Trypsin-FITC@MIL-101 (Cr)
Figure 5:
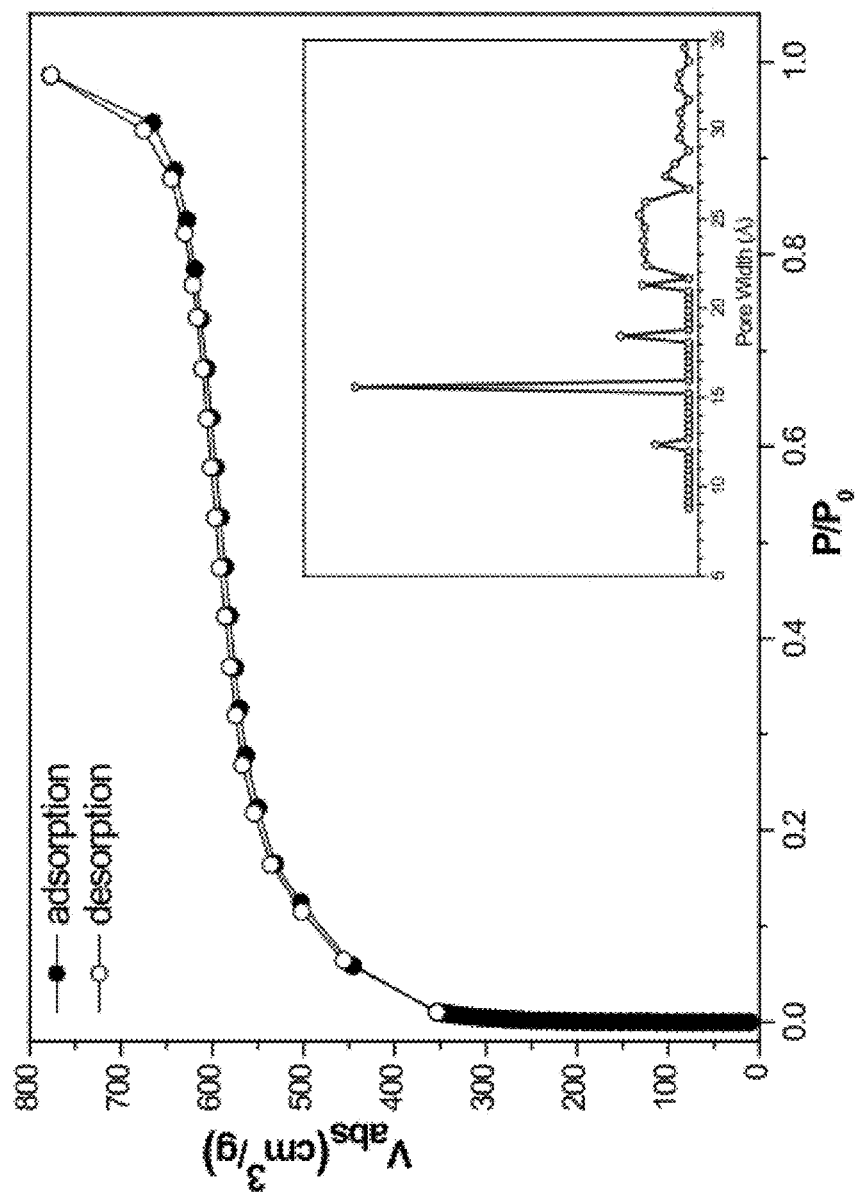
FIG. 5 is a nitrogen adsorption-desorption curve analysis chart showing of CYCU-4 porous support material showing the relationship between the capability of nitrogen adsorption-desorption and the pore size distribution.

The structure of CYCU-4 is illustratively shown in FIG. 3. CYCU-4 has 2.1 nm rhomboidal pores with lamellar crystal sizes ranging from 100 to 1000 nm as shown in FIG. 4(a). In general, the topology and structure of CYCU-4 is thermally stable up to approximately 300° C. Refer to FIG. 5, according to the results of $N_2$ adsorption isotherm using the density functional method, CYCU-4 has the low pressure $N_2$ adsorption related characteristic, and its revealed microporous characteristics with pore size distributions of approximately 12, 16, 18, and 21 Å (also refer to the FIG. 4(a)). The surface areas and pore volumes gave CYCU-4 a Brunauer-Emmett-Teller (BET) surface area of 1910 m2/g. Langmuir surface area of CYCU-4 is 2671 m2/g. The analysis results obviously show that CYCU-4 has microporous characteristics.

Embodiment 2

Assaying the Structural Resistance of CYCU-4 Against Different Solvents

The structural resistance of CYCU-4 against different solvents are assayed by storing the desolvated sample in solvents including dimethylformamide (DMF), N,N-diethylformamide (DEF), toluene and methanol at room temperature for 7 days. The results are shown in FIG. 4, which demonstrates the structural resistance of CYCU-4 against different solvents. Specifically, the porous CYCU-4 remains unaltered and kept some of its crystallinity, but with decreased porosity, and is transformed into a more mesoporous structure. When CYCU-4 is disposed in an aqueous solution and stored at room temperature for 1 h, mesopores ranging from 3 to 5.0 nm are created. The aforesaid assay is the well-known in the art, and it is no described in detail herein.

Therefore, CYCU-4 MOF displays microporous properties in the desolvated form and transformed into a mesoporous structure upon soaking in organic solvents or aqueous solution. The combination of micropores and mesopores formed in this MOF also provide potential of being widely used for various potential applications, preferably as being the porous support materials of solid carriers to immobilize biocatalysts (e.g., the FITC-labeled trypsin) to form the bioreactor and to further accomplish the biocatalysis system according to the present invention.

TABLE 4

Nitrogen adsorption and desorption isotherms of selected CYCU-4 and

| MOFs | BET surface area ($cm^2 g^{-1}$) | Langmuir surface area ($cm^2 g^{-1}$) | Pore size (nm) |
|---|---|---|---|
| MIL-101(Cr) | 2939 | 3938 | 1.2[b] |
| FITC@MIL-101(Cr) | 2554 | 3409 | 1.2 |
| Trypsin-FITC@MIL-101(Cr) | 2802 | 3747 | 1.2 |
| CYCU-4 | 1910 | 2671 | 1.2-2.1[b] |
| FITC@CYCU-4 | 51.87 | 73.19 | 3.0-5.0 |
| Trypsin-FITC@CYCU-4 | 33.75 | 66.89 | 3.0-5.0 |

[a] Measurement at 77K;
[b]Window pore size;
[c]Material was desolvated.

Embodiment 3

Preparation of MIL-101

Another preferred embodiment of the present invention is Trypsin-FITC@MIL-101(Cr) bioreactor, wherein the MOF, MIL-101(Cr), is $[Cr_3O(BDC)_3(F)(H_2O)_2] \cdot 25H_2O$. MIL-101(Cr) is prepared in accordance with the method proposed by Férey, G. et al. (published in Science 2005, 309, 2040.). In brief, MIL-101(Cr) of the present invention are synthesized by hydrothermal synthesis method, in which chromium nitrate nonahydrate, $(Cr(NO_3)_3 \cdot 9H_2O$, 400 mg, 1.0 mmol), terephthalic acid ($C_8H_6O_4$, 166 mg, 1.0 mmol), hydrofluoric acid (HF, 0.2 ml) and water (5 ml) are mixed and then disposed in a 23-ml teflon-autoclave for heating reaction, and the heating reaction under 220° C. sustains for 8 h to generate product in green powder. The product is collected, filtered and washed by pure water and ethanol at room temperate. Then, this product is heated in DMF for 1 day, and following a step of stirring in ethanol overnight for activation. The activated MIL-101 (Cr) product is finally dried in vacuum and then heated at temperate 150° C. for 1 day for the follow-up procedures for forming the bioreactor. The method for preparing Trypsin-FITC@MIL-101(Cr) bioreactor is essentially the same as the method of aforementioned Trypsin-FITC@CYCU-4 bioreactor, thus it is not described herein.

Embodiment 4

Trypsin-FITC Conjugation and Immobilization onto MOFs

First, the following three solution are vortex-mixed gently: (1) 50 μl of 6000 ug/ml TPCK-treated trypsin standard stock solution in which trypsin has been treated by TPCK [L-(tosylamido-2-phenyl) ethyl chloromethyl ketone]; (2) 50 μd FITC (5 mM) and (3) 50 μl sodium carbonate buffer solution (100 mM); and a homogenous mixture are formed. The homogenous mixture is placed in a beaker with room temperature water and then microwave-heated for 2 min (180 W, SAMPO domestic microwave oven model RE-1002SM) to link the FITC with trypsin to form the Trypsin-FITC absorbent in solution form. Then immobilizing the Trypsin-FITC onto the specific native MOFs (1 mg) (i.e., CYCU-4 or MIL-101(Cr)) by suspending the MOFs in a 100 μl Trypsin-FITC solution, and then gently vortex the suspension at room temperature for 30 min to form Trypsin-FITC@MOF. The Trypsin-FITC@MOF product is washed three times with 100 μl phosphate buffer prior to further digestion or submission to other tests.

Embodiment 5

BSA Denaturation

The BSA ligand is denatured prior to the real catalytic hydrolysis, which is a common step in the art. Thus, according to the preferred embodiment of the present invention, the steps of BSA denaturation are briefly described herein. Firstly, a 10 mg of lyophilized BSA protein is resuspended in a 1 ml aqueous solution composed of urea (6 M) and Tris buffer (100 mM) to form the BSA solution. A 5 μl of dithiothreitol (DTT) reducing reagent (200 mM) is added to a 100 μl aliquot of the BSA solution (10 mg/mL) in a 1.5-ml plastic micro-centrifuge tube and vortex-mixed gently. The mixture is allowed to stand at room temperature for 1 h. Then, a 20 μl of alkylating reagent, iodoacetamide (IAA, 200 mM), is added into the above mixture with a gentle vortex, and then the alkylation process is proceeded at room temperature in the dark for 1 h. After the alkylation process, in order to consume the unreacted IAA, 20 μl of DTT reducing agent is further added into the reaction solution with gentle vortex, and this reaction sustains at room temperature for 1 h. The subsequent solution is mixed with 775 μl of D.I. water to reduce the urea concentration to around 0.6 M that the trypsin can retain its activity.

Embodiment 6

BSA Digestion via Trypsin-FITC@MOFs

The denatured BSA solution (100 μl) is added into and mixed with the Trypsin-FITC@MOF bioreactor with gentle vortex, and then an ultrasonic-assisted digestion reaction is carried out for 2 min to obtain the peptide solution. The peptide solution is separated from the solid Trypsin-FITC@MOF bioreactor by 5-min centrifugation. Acetic acid solution (1 μl, 17.4 M) is added to stop the digestion reaction. The subsequent acidified supernatant is desalted using ZIP-TIP-C18 following the manufacturer's instruction to obtain the peptide solution. The peptide solution is diluted with ammonium acetate solution (50 mM, pH 8.75) containing 5% ACN prior to nano-LC-MS to form peptide digests.

Embodiment 7

Nano-LC-MS Analysis Method

According to the method proposed by Hsu et al (Journal of Chromatography A 2011, 1218, 350.) with minor modification, a poly(stearyl methacrylate-divinyl benzene-vinylbenzyltrimethylammouium), abbreviated in "poly(SMA-DVB-VBTA)" monolithic separation column (70 cm length; 75 μm I.D.) are used as separation column for nano-LC-MS. The column is equilibrated with 100% solvent A (A: 95% water, 5% ACN, 0.1% FA, v/v). BSA peptide digests are separated in the following gradient mode: 0-10 min with 100% A; 10-60 min with 100%-30% A; 60-65 min with 30%-0% A, with solvent B (B: 20% water, 80% ACN, 0.1% FA, v/v) at a flow rate of 250 nl/min. The sample 0.5 μl is injected via an autosampler (Dionex) with a 1 μl sample loop. The Nano-LC-ESI-MS is performed on a UltiMate 3000 Nano-LC system (Dionex, Amsterdam, The Netherlands) coupled to the amazon SL mass spectrometer (Bruker-Daltonik, Germany) equipped with a nanoelectrospray ionization source (Bruker). All devices are controlled using HyStar 3.2 (BrukerDaltonik). Other related detail conditions or procedures are known skills or techniques in the art and it is not described herein. Particularly, the data analysis is conducted in accordance with the Mascot database, and the analyzed data is aligned and compared with the correspondent sequences in Mascot database. More specifically, the peptide fragment fingerprint analysis for protein identification is performed with BioTools 3.1 (BrukerDaltonik) using the Mascot database, and the data is consequently calculated to obtain the ratio of "sequence coverage".

Embodiment 8

Determination of Trypsin Activity and Loading Capacity of Trypsin-FITC@CYCU-4

The activities of immobilized trypsin of Trypsin-FITC@CYCU-4 bioreactor are evaluated by the capacity of hydrolyzing N-α-benzoyl-DL-arginine (BAPNA) to form the product of hydrolysis, p-nitroaniline, and the product amounts can be quantified by measuring the absorbance at 405 nm with a spectrophotometer. Practically, the 500 μl 1 mM BAPNA solution in 10 mM sodium phosphate buffer (pH 7.9) is added to the Trypsin-FITC@CYCU-4 suspension. After 15 min, the Trypsin-FITC@CYCU-4 is separated by centrifugation and the absorbance of the supernatant is measured at 405 nm with spectrophotometer. And the data collected can be quantified to represent the activity of trypsin.

Similarly, the loading capacity of CYCU-4 for Trypsin-FITC is evaluated by fluorescence emission method or activity test method of BAPNA hydrolysis depending on detecting the fluorescence emission of hydrolyzed product. As to the fluorescence emission method, it depends on measuring the difference in the fluorescence emission intensity of Trypsin-FITC solution before and after immobilization into CYCU-4 is used to determine the concentration of Trypsin-FITC adsorbed on CYCU-4. After calibrating the solution volume (500 μl) and the initial trypsin concentration (2000 μg/mL), the calculated loading capacity of Trypsin-FITC@CYCU-4 is about 55.2 μg trypsin/mg MOF. Additionally, as to the activity test method of BAPNA hydrolysis, the UV absorbance of the hydrolysis product (p-nitroaniline) Trypsin-FITC@CYCU-4 and free trypsin (2000 ppm trypsin in-solution) is respectively measured and compared, and the ratio of the measured data is used to represent the loading capacity of tested material (i.e., Trypsin-FITC@CYCU-4 or free trypsin); and according to the embodiment, the approximate loading capacity of Trypsin-FITC@CYCU-4 is around 63.2 μg trypsin/mg MOF, which is close to the results from the fluorescence emission method.

Embodiment 9

Characterization of CYCU-4 and MIL-101(Cr)

Figure 6:
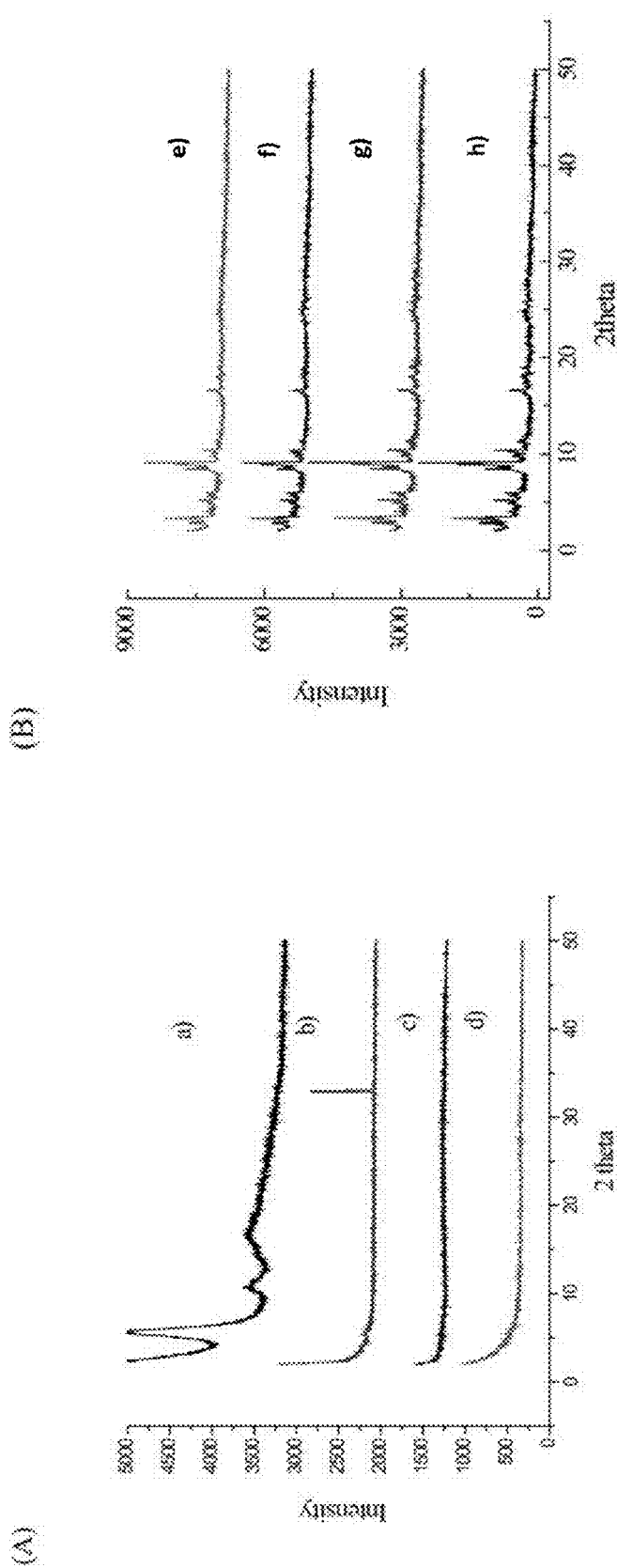
FIG. 6 is a diagram of X-ray diffraction analysis (powder X-ray diffraction, PXRD). (A) X-ray diffraction analysis of CYCU-4 system; (B) X-ray diffraction analysis of MIL-101 (Cr) system; (a) CYCU-4 at initial state; (b) CYCU-4 after being soaked in sodium carbonate solution; (c) FITC@CYCU-4; (d) Trypsin-FITC@CYCU-4; (e) MIL-101 (Cr) at initial state; (f) MIL-101(Cr) after being soaked in sodium carbonate solution; (g) FITC@MIL-101(Cr); (h) Trypsin-FITC@MIL-101(Cr)

The preferable MOFs (CYCU-4 and MIL-101) are characterized by scanning electron microscopy (SEM). The appearance and the size of CYCU-4 and MIL-101 are shown in FIG. 4. Those MOFs are characterized to evaluate the effects derived from the biomolecule immobilization method. As shown in FIG. 4, CYCU-4 and MIL-101 both successfully immobilizes the Trypsin-FITC by the biomolecule immobilization method of the present invention. Refer to FIG. 6 showing the powder X-ray diffraction (PXRD) analysis results for the preferable CYCU-4 and MIL-101(Cr) bioreactor, the corresponding intermediates and the products (i.e., Trypsin-FITC @ CYCU-4 and Trypsin-FITC @ MIL-101 (Cr)). According to FIG. 4, the panel e), f), g), h) and FIG. 6 panel (B) showing that inherent characteristic and appearance of MIL-101(CR) still remain intact after immobilizing Trypsin-FITC, but the aggregation phenomenon indicates the rigidity and structure stability of MIL-101 (Cr). However, according to FIG. 4, panel a), b), c), d) and FIG. 6 panel (A), changes are observable on CYCU-4 after immobilizing Trypsin-FITC, specifically, the reduced crystalline properties and apparent formation of mesopores are observed (as shown in FIG. 5).

Figure 7A:
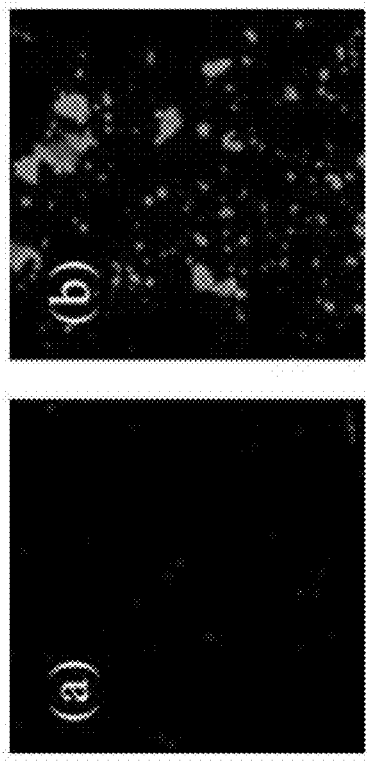
FIG. 7A shows images of confocal laser scanning microscopy (CLSM). (a) CYCU-4 at initial state; (b) Trypsin-FITC@ CYCU-4.
Figure 7B:
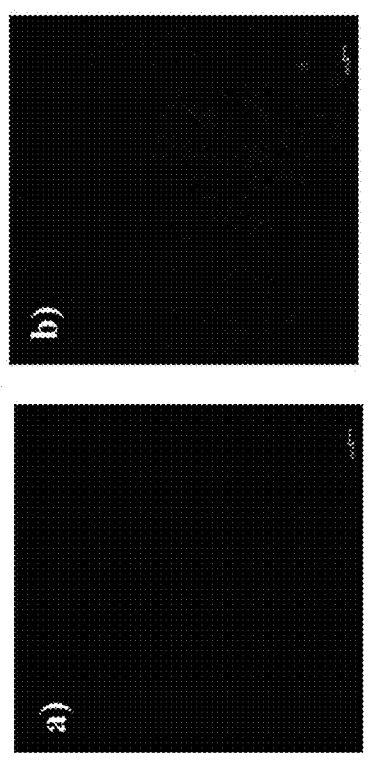
FIG. 7B shows images of confocal laser scanning microscopy (CLSM). (a) MIL-101(Cr) at initial state; (b) Trypsin-FITC@MIL-101(Cr).

Because FITC has excitable fluorescence property (excitation wavelength generally ranges from 450 nm-488 nm), the immobilization capacities of CYCU-4 and MIL-101(Cr) on Tryspin-FITC can be confirmed through emissive fluorescence. For example, confocal laser scanning microscopy (CLSM) is used for monitoring the profile of FITC molecule that enters into MOF. Practically, a slight auto-fluorescence is observed in CYCU-4 which is absent in MIL-101(Cr). As Trypsin-FITC being adsorbed and entered into MOF successfully, the fluorescence signal is increased. In other words, the widely dispersed fluorescence over the MOF particles indicates successful loading of FITC. CYCU-4 system is the MOF most significantly showing this phenomenon, as shown in FIG. 7A, and FIG. 7B.

On the other hand, CLSM analysis with Argon laser beam can adjust z axial position to excite Trypsin-FITC to emit fluorescent in different depth, so as to detect the fluorescence signal at different depth and observe layer-by-layer distribution of FITC and Trypsin-FITC inside the MOF particles. Comparison of these CLSM micrographs and their 3D images constructed based on a hundred z axial slices, it indicates that almost the same fluorescence distribution along the different depths of the MOF solids, which accounts for the high dispersion of Trypsin-FITC not only on the MOF surface but also throughout the MOF particles therein.

Moreover, according to aforesaid results, the structure of porous support material constructed by CYCU-4 system is changed gradually with the adsorption process, while this phenomenon shows no significant effect on the characteristic or capacity for immobilized Trypsin-FITC. According to Table 4 summarizing the porous structure related characteristics (the surface areas and the pore sizes) of MOFs (native MOFs, FITC@MOFs and Trypsin-FITC@MOFs), even though the structure of CYCU-4 is changed with the its environment, the morphological conversion rarely affects FITC adsorption capacity.

In addition, with FITC or Trypsin-FITC adsorption, CYCU-4 has a marked decrease in the surface area (97.3% and 98.2% for FITC@CYCU-4 and Trypsin-FITC@CYCU-4, respectively), which confirmed that the FITC adsorption in CYCU-4 solids is not affected by the trypsin bonding to FITC. Obviously, the native form of CYCU-4 has significant microporous properties, which give an excellent adsorption capacity of FITC. After treatment with FITC, the structure of CYCU-4 is transformed accompanied by aggregation and subsequently produced mesopores, which means the microporous gradually transforms to generate mesoporous structure and the properties thereof. This structural change may leave some free space or provide an adequate space to accommodate trypsin macromolecules and further enhance Trypsin-FITC immobilization on this MOF. Accordingly, these unusual mesopores make CYCU-4 capable of loading more trypsin macromolecules. On the other and, the transformed type of CYCU-4 are prepared by using CYCU-4 as the raw material with alternative preparation approach. The transformed CYCU-4 has no microporous properties (non-porous) and crystallinity. In comparison with the porous CYCU-4, the transformed CYCU-4 shows much poorer performance for entrapping FITC, loading Trypsin-FIC, trypsin hydrolytic activity and reusability, as shown in Table 1 and Table 2. Therefore, appropriate microporous properties and crystallinity are essential for the excellent performance of Trypsin-FITC@CYCU-4.

As for MIL-101(Cr) system, the pore sizes are retained but a slight decrease in the surface area is observed after FITC or Trypsin-FITC adsorption (13% and 4.7% decrease for FITC@MIL-101(Cr) and Trypsin-FITC@MIL-101(Cr), respectively). As previously described, the MIL-101(Cr) has the highest FITC loading capacity but exhibited poorer reusability that no BSA digestion ability for the third reuse of FITC@MIL-101(Cr). It is possibly due to the nearly similar sizes between the FITC molecule and the window formed in MIL-101(Cr), thus a significant decrease (13%) in the surface area after FITC capture. However, once trypsin is bonded to FITC, this macromolecule could hinder FITC moiety to enter the MIL-101(Cr) window with minor surface area reduction thereby accounting for the lower trypsin-FITC absorption capacity which further reduces the biocatalysis efficiency and the reusability.

Therefore, according to above the description and the embodiments of the present invention, an improved method for immobilizing macromolecules on MOF is provided. Compared to the conventional immobilization methods that generally requires hours of time for processing, the molecule immobilization method according to the present invention requires apparently shortened time duration and simple procedure. Specifically, the molecule immobilization method advantageously utilizes a vortex process and a shortened immobilization time for 15 minutes to 60 minutes to accomplish the immobilization effectively; and to subsequently form the effective bioreactor and the biocatalysis system. A detail comparison regarding the approaches and corresponding immobilization efficiency between the present invention and the conventional techniques in the art is shown in Table 5.

TABLE 5

Listing of current solid carriers and the bioreactor of the present inveniton for immobilizing trypsin

| Reference | Materials | Modification | Time of surface modification | Time of trypsin immobilization | Sequence coverage/ matched peptides |
|---|---|---|---|---|---|
| Present invention | MOFs | NA | NA | Trypsin adsorption/immobilization: 30 min | BSA: 72% |
| B. Lee, et al. Proteomics 2011, 11, 309. | Silica-coated magnetic nano-particles (NPs) | Functional group | Amino-functionalized: 3 h | Trypsin coating: 27 h | BSA: 50% Ovalbumin: 80% Myoglobin: 80% Carbonic anhydrase: 80% Lactoglobulin: 50% |
| S. Lin, et al. Journal of Proteome Research 2008, 7, 1297. | Magnetic Nanoparticles | Functional group | Amino-functionalized: 6 h Aldehyde-functionalized: 1.5 h Total :7.5 h | Trypsin covalently binding: 4 h | BSA: 38% Myoglobin: 80% Cytochrome c: 76% |
| F. Casadonte, et al. Chem. Eur. J. 2010, 16, 8998. | Mesoporous Silica (SBA-15) | Functional group | N-(2-Aminoethyl)-3-aminopropyl-functionalized: 18 h | Trypsin adsorption: 10 min | Myoglobin: 100% |
| L. Qiao, et al. Chem. Eur. J. 2008, 14, 151. | Mesoporous silicate | Functional group | Cyano-functionalized: 30 h | Trypsin adsorption: 16 h | Cytochrome c: 63% |
| J. Sproβ and A. Sinz, Anal. Chem. 2010, 82, 1434. | Polymer monolith | Functional group | Aldehyde functionalization: 8 h | Trypsin covalently binding: 30 h | BSA: 41% |
| E. Calleri, et al., J. Chromatogr. A 2011, 1218, 8937. | Polymer monolith | Epoxy organic monoliths polymerization | few min | Trypsin covalently binding: 26 h | Human serum albumin(HSA): 78% Bovine ribonuclease B (RNaseB): 80% β-Casein: 49.76% |
| G. Bayramoğlu, et al. Biochemical Engineering Journal 2008, 40, 262. | Polymer grafted magnetic beads | Graft copolymerization of methacrylic acid | 60 h | Trypsin covalently binding: 3 h | Cytochrome c: 28% HSA: 20% |
| Y. Deng, et al. Adv. Mater. 2009, 21, 1377. | Core/shell colloidal magnetic zeolite microspheres | Zeolite surface modification | 3 day | Trypsin adsorption: 1 h | BSA: 25% Myoglobin: 89% Cytochrome c: 77% |

What is claimed is:

1. A molecule immobilization method of immobilizing a biomolecule to perform a biocatalysis, comprising the following steps of: providing the biomolecule and a small molecule which leads the biomolecule, and linking the biomolecule and the small molecule by microwave to form an adsorbent;
providing a porous support material, and mixing the porous support material and the adsorbent to form a mixture; and
treating the mixture by a vortex process such that the adsorbent being diffused and immobilized on the porous support material to form a bioreactor.

2. The molecule immobilizing method of immobilizing a biomolecule to perform a biocatalysis according to claim 1, wherein the biomolecule is a protein enzyme; the small molecule is a dye; and the porous support material is a metal organic framework.

3. The molecule immobilizing method of immobilizing a biomolecule to perform a biocatalysis according to claim 1, wherein a first duration of linking the biomolecule and the small molecule by microwave ranges from 1 minute to 5 minutes.

4. The molecule immobilizing method of immobilizing a biomolecule to perform a biocatalysis according to claim 1, wherein a second duration of the vortex process ranges from 10 minutes to 60 minutes.

5. The molecule immobilizing method of immobilizing a biomolecule to perform a biocatalysis according to claim 2, wherein the metal organic framework is an aluminum mental-organic framework material, and the aluminum mental-organic framework materials has a pore size ranging from 0.8 nm to 2.1 nm.

6. The molecule immobilizing method of immobilizing a biomolecule to perform a biocatalysis according to claim 2, wherein the dye is fluorescein isothiocyanate.

7. The molecule immobilizing method of immobilizing a biomolecule to perform a biocatalysis according to claim 2, wherein the protein enzyme is trypsin.

\* \* \* \* \*